United States Patent [19]

Minai et al.

[11] Patent Number: 4,608,442
[45] Date of Patent: Aug. 26, 1986

[54] PROCESS FOR PREPARING 4-HYDROXY-2-CYCLOPENTENONES

[75] Inventors: Masayoshi Minai, Moriyama; Tadashi Katsura, Suita, both of Japan

[73] Assignee: Sumitomo Chemical Company, Limited, Osaka, Japan

[21] Appl. No.: 629,488

[22] Filed: Jul. 10, 1984

[30] Foreign Application Priority Data

Jul. 22, 1983 [JP]  Japan ................................ 58-134867

[51] Int. Cl.$^4$ ............................................. C07C 45/65
[52] U.S. Cl. ................................................... 568/346
[58] Field of Search ............... 568/341, 346, 314, 906, 568/347

[56] References Cited

U.S. PATENT DOCUMENTS

| | | | |
|---|---|---|---|
| 2,435,078 | 1/1948 | Hearne et al. | 568/906 |
| 3,355,505 | 11/1967 | Tedeschi | 568/906 |
| 3,925,485 | 12/1975 | Chabardes et al. | 568/341 |
| 4,006,193 | 2/1977 | Ninagawa et al. | 568/906 |
| 4,347,386 | 8/1982 | Saito et al. | 568/341 |
| 4,496,767 | 1/1985 | Minai et al. | 568/346 |

OTHER PUBLICATIONS

Floyd, J. Org. Chem., vol. 43, #9, pp. 1641–1643 (1978).
Young et al, J.A.C.S., vol. 73, pp. 780–782 (1951).
Dimroth, Berichte, vol. 71, pp. 1333–1345 (1938).
Braude, Quarterly Review, vol. 4, pp. 404–417 (1950).

*Primary Examiner*—James H. Reamer
*Attorney, Agent, or Firm*—Birch, Stewart, Kolasch & Birch

[57] ABSTRACT

A process for producing a compound of the formula:

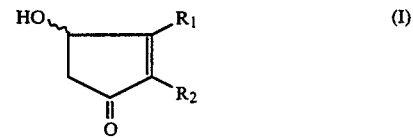

(I)

wherein $R_1$ is a hydrogen atom, an alkyl group or an alkenyl group and $R_2$ is an alkyl group, an alkenyl group or an alkynyl group, which comprises treating a compound of the formula:

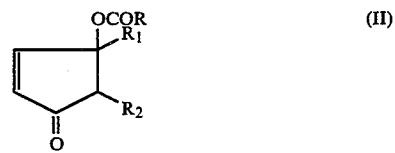

(II)

wherein $R_1$ and $R_2$ are each as defined above and R is a hydrogen atom or a lower alkyl group in the presence of an acidic substance and water.

10 Claims, No Drawings

PROCESS FOR PREPARING 4-HYDROXY-2-CYCLOPENTENONES

The present invention relates to a process for preparing 4-hydroxy-2-cyclopentenones. More particularly, it relates to a process for preparing 4-hydroxy-2-cyclopentenones of the formula:

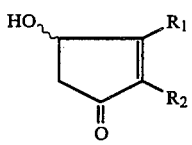

wherein $R_1$ is a hydrogen atom, an alkyl group or an alkenyl group and $R_2$ is an alkyl group, an alkenyl group or an alkynyl group from the corresponding 2-acyloxy-4-cyclopentenones of the formula:

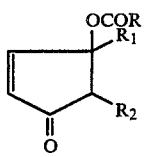

wherein $R_1$ and $R_2$ are each as defined above and R is a hydrogen atom or a lower alkyl group in a single step.

In the above significances, the terms "alkyl", "alkenyl" and "alkynyl" are intended to mean those having not more than 12 carbon atoms. The term "lower alkyl" is intended to mean not more than 6 carbon atoms.

Said 4-hydroxy-2-cyclopentenones (I) are useful as intermediates in the synthesis of agricultural chemicals, pharmaceuticals, perfumes, etc. For instance, they can be employed as intermediates for the synthesis of chrysanthemic esters which are useful as pyrethroidal insecticides.

For the rearrangement of 4-cyclopentenones, there is known the procedure as shown in the formulas [Tetrahedron, 35, 135 (1975); Heterocycles, 19, 1735–1744 (1982)]:

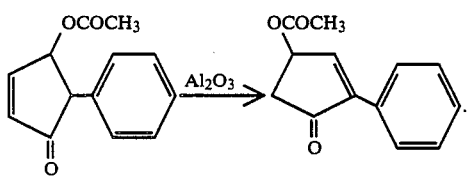

However, this procedure is the rearrangement of esters into other esters, and the yields are low. Further, it is never known whether the rearrangement as above can take place on 4-cyclopentenones wherein the substituent at the 2-position is other than phenyl (e.g. alkyl, alkenyl, alkynyl). Even if the rearrangment takes place, the hydrolysis of the produced esters to the corresponding free acids is necessary for the utilization as agricultural chemicals. This hydrolysis would reduce the yields of the desired free acids.

The process of this invention can provide the objective 4-hydroxy-2-cyclopentenones (I) from the corresponding 2-acyloxy-4-cyclopentenones (II) in a single step with good yields and high purities. Further, it is possible to carry out such conversion simultaneously with racemization.

According to the present invention, the 2-acyloxy-4-cyclopentenone (II) is treated with water in the presence of an acidic substance to give the corresponding 4-hydroxy-2-cyclopentenone (I).

The starting 2-acyloxy-4-cyclopentenone (II) in dl-form is known or can be produced by a conventional procedure [Japanese Patent Publn. (unexamined) No. 88341/83]. (Treatment of the) 2-acyloxy-4-cycolopentenone (II) in dl-form with any appropriate enzyme affords the corresponding optically active one, i.e. d-form or l-form [EP 0080671A].

Examples of the starting 2-acyloxy-4-cyclopentenone (II) are 3-acetoxy-2-methyl-4-cyclopentenone, 3-acetoxy-2-ethyl-4-cyclopenteneone, 3-acetoxy-2-n-propyl-4-cyclopentenone, 3-acetoxy-2-isopropyl-4-cyclopentenone, 3-acetoxy-2-n-butyl-4-cyclopentenone, 3-acetoxy-2-n-pentyl-4-cyclopentenone, 3-acetoxy-2-n-hexyl-4-cyclopentenone, 3-acetoxy-2-n-heptyl-4-cyclopentenone, 3-acetoxy-2-allyl-4-cyclopentenone, 3-acetoxy-2-(2-cis-butenyl)-4-cyclopentenone, 3-acetoxy-2-(w-butenyl)-4-cyclopentenone, 3-acetoxy-2-(2-cis-pentenyl)-4-cyclopentenone, 3-acetoxy-2-(2-transpentenyl)-4-cyclopentenone, 3-acetoxy-2-(3-cis-hexenyl)-4-cyclopentenone, 3-acetoxy-2-propargyl-4-cyclopentenone, 3-acetoxy-2-(2-pentynyl)-4-cyclopentenone, 3-acetoxy-2-(α-methylallyl)-4-cyclopentenone, 3-acetoxy-2-(1-cyclopentenyl)-4-cyclopentenone, 3-acetoxy-2-cyclohexyl-4-cyclopentenone, 3-acetoxy-2,3-dimethyl-4-cyclopentenone, 3-acetoxy-2-ethyl-3-methyl-4-cyclopentenone, 3-acetoxy-2-n-propyl-3-methyl-4-cyclopentenone, 3-acetoxy-2-isopropyl-3-methyl-4-cyclopentenone, 3-acetoxy-2-n-butyl-3-methyl-4-cyclopentenone, 3-acetoxy-2-n-pentyl-3-methyl-4-cyclopentenone, 3-acetoxy-2-n-hexyl-3-methyl-4-cyclopentenone, 3-acetoxy-2-n-heptyl-3-methyl-4-cyclopentenone, 3-acetoxy-2-allyl-3-methyl-4-cyclopentenone, 3-acetoxy-2-(2-cis-butenyl)-3-methyl-4-cyclopentenone, 3-acetoxy-2-(ω-butenyl)-3-methyl-4-cyclopentenone, 3-acetoxy-2-(2-cis-pentenyl)-3-methyl-4-cyclopentenone, 3-acetoxy-2-(2-trans-pentenyl)-3-methyl-4-cyclopentenone, 3-acetoxy-2-(3-cis-hexenyl)-3-methyl-4-cyclopentenone, 3-acetoxy-2-propargyl-3-methyl-4-cyclopentenone, 3-acetoxy-2-(2-pentynyl)-3-methyl-4-cyclopentenone, 3-acetoxy-2-(α-methylallyl)-3-methyl-4-cyclopentenone, 3-acetoxy-2-(1-cyclopentenyl)-3-methyl-4-cyclopentenone, 3-acetoxy-2-cyclohexyl-3-methyl-4-cyclopentenone, etc. Further examples of the 2-acyloxy-4-cyclopentenone (II) are those as exemplified above but having a different acyloxy group (e.g. formyloxy, propionyloxy, butyryloxy) at the 3-position in place of the acetoxy group. Those as exemplified above may be optically active or racemic.

The acidic substance may be an inorganic acid or an organic acid. Specific examples are hydrochloric acid, sulfuric acid, nitric acid, phosphoric acid, chloric acid, polyphosphoric acid, boric acid, toluenesulfonic acid, methanesulfonic acid, acetic acid, etc. The amount of the acidic substance is usually from 0.005 to 100 moles, preferably from 0.2 to 50 moles, to one mole of the 2-acyloxy-4-cyclopentenone (II).

Water is normally used in an equimolar or more amount to the 2-acyloxy-4-cyclopentenone (II). In case of using an organic carboxylic acid as the acidic substance, however, water may be preferably used in an amount of not less than 3 moles, particularly of not less than 5 moles, to one mole of the 2-acyloxy-4-cyclopentenone (II). No upper limit is present on the amount of water, but it may be practically up to about 50 moles.

Water can also serve as the reaction medium. When desired, however, any solvent inert to the reaction may beadditionally used as the reaction medium. Examples of such inert solvent are hydrocarbons (e.g. n-hexane, benzene, toluene), halogenated hydrocarbons (e.g. dichloromethane, chloroform), ethers (e.g. diethyl ether, tetrahydrofuran, dioxane), ketones (e.g. acetone), dimethylsulfoxide, dimethylformamide, etc. They may be used solely or in combination.

The reaction temperature may be usually within a range of −40° to 130° C., preferably of −20° to 110° C. No particular limitation is present on the reaction period of time.

As a result of the above reaction, there is obtained the reaction mixture comprising the objective 4-hydroxy-2-cyclopentenone (I) produced in a good yield. By application of a conventional separation procedure such as extraction, fractionation, concentration and distillation to the reaction mixture, the 4-hydroxy-2-cyclopentenone (I) can be recovered with a high purity.

During the above reaction, racemization can proceed simultaneously. When, therefore, the starting 4-hydroxy-2-cyclopentenone (II) is optically active, the objective 4-hydroxy-2-cyclopentenone (I) is obtainable in the form of racemic mixture. It is frequently observed that an optically active form (e.g. d-form) of the 4-hydroxy-2-cyclopentenone (II) is useful, while the other optically active form (e.g. l-form) is useless. Said racemization is quite advantageous for conversion of the useless form into the useful form, although the product is a racemic mixture. Still, the racemic mixture as herein obtained is not a real racemic mixture which contains d-form and l-form in an equal amount but a mixture of d-form and l-form, one of them being contained in a slightly excessive amount in comparison with the other. Thus, the product shows a slightly positive or negative optical rotation. Since, however, the excessive extent is so small that the product may be considered substantially as a racemic mixture.

Practical and presently preferred embodiments of the invention are illustratively shown in the following Examples wherein part(s) and % are by weight unless otherwise indicated.

EXAMPLE 1

Into a four-necked flask equipped with a stirrer and a thermometer, 5% sulfuric acid (10 ml) was charged, and dl-3-acetoxy-2-allyl-3-methyl-4-cyclopentenone (2 g) was dropwise added thereto in 1 hour while keeping the inner temperature at 30° to 50° C. After completion of the dropwise addition, the resultant mixture was kept at the same temperature as above for 3 hours. Thereafter, sodium chloride (3 g) was added to the reaction mixture, which was extracted with methyl isobutyl ketone (20 ml) three times. The organic layer was washed with a saturated aqueous sodium chloride solution, and methyl isobutyl ketone was removed by distillation. The residue was purified by column chromatography to give 1.27 g of 2-allyl-4-hydroxy-3-methyl-2-cyclopentenone. Yield, 84%.

In the same manner as above but using an aqueous solution of the acidic substance as shown in Table 1 (10 ml) instead of 5% sulfuric acid (10ml), the reaction was carried out to give 2-allyl-4-hydroxy-3-methyl-2-cyclopentenone in the yield as shown in Table 1.

TABLE 1

| Aqueous solution of the acidic substance | Yield (%) |
|---|---|
| 10% Hydrochloric acid | 85 |
| 10% p-Toluenesulfonic acid | 81 |
| 5% Nitric acid | 82 |

EXAMPLE 2

In the same flask as in Example 1, l-3-acetoxy-2-allyl-3-methyl-4-cyclopentenone (1.94 g; optical rotation $[\alpha]_D^{20} -93.6°$ (c=1, chloroform)) and 10 % sulfuric acid (20 ml) were charged, and the resultant mixture was stirred at 60° C. for 8 hours. After completion of the reaction, the reaction mixture was subjected to post-treatment and purification as in Example 1 to give 1.23 g of 2-allyl-4-hydroxy-3-methyl-2-cyclopentenone. Yield, 81%. Optical rotation, $[\alpha]_D^{20} -1.1°$ (c=1, chloroform).

EXAMPLES 3 TO 7

In the same manner as in Example 2 but using the 2-acyloxy-4-cyclopentenone (II) as shown in Table 2 instead of l-3-acetoxy-2-allyl-3-methyl-4-cyclopentenone, the reaction was carried out. The results are shown in Table 2.

TABLE 2

| Example No. | Starting 2-acyloxy-4-cyclopentenone (II) | | | | | Objective 4-hydroxy-2-cyclopentenone (I) | | |
|---|---|---|---|---|---|---|---|---|
| | R | $R_1$ | $R_2$ | $[\alpha]_D^{20}$ | Amount (g) | Amount (g) | Yield (%) | $[\alpha]_D^{20}$ |
| 3 | —OCOCH$_3$ | —CH$_3$ | —CH$_2$C≡CH | −16.2° | 1.92 | 1.22 | 81.3 | −1.8° |
| 4 | —OCOCH$_3$ | —CH$_3$ | —n-C$_5$H$_{11}$ | −69.4° | 2.24 | 1.54 | 84.5 | −1.4° |
| 5 | —OCOCH$_3$ | —CH$_3$ | —CH$_3$ | −20.7° | 1.68 | 1.03 | 82 | −1.2° |
| 6 | —OCOCH$_3$ | —H | —n-C$_5$H$_{11}$ | +112.0° | 1.78 | 1.13 | 83 | −2.4° |
| 7 | —OCOCH$_3$ | —H | —CH$_2$CH=CH$_2$ | +68.8° | 1.80 | 1.15 | 83.5 | −2.1° |

EXAMPLE 8

In the same flask as in Example 1, 10% aqueous hydrochloric acid (10 ml) and dioxane (10 ml) were charged, and d-2-allyl-3-acetoxy-3-methyl-4-cyclopentenone (1.94 g; optical rotation, $[\alpha]_D^{20} +91.88°$ (c=1, chloroform)) was dropwise added thereto in 2 hours while keeping the inner temperature at 40° to 50° C. After completion of the dropwise addition, the resultant mixture was stirred at the same temperature as above for 3 hours. The reaction mixture was subjected to post-treatment and purification as in Example 1 to give 1.29 g of 2-allyl-3-methyl-4-hydroxy-2-cyclopentenone. Yield, 85%. Optical rotation, $[\alpha]_D^{20} +1.0°$ (c=1, chloroform).

In the same manner as above but using tetrahydrofuran (10 ml) instead of dioxane ( 10 ml), there were obtained 1.31 g of 2-allyl-3-methyl-4-hydroxy-2- cyclopentenone. Yield, 86%. Optical rotation, $[\alpha]_D^{20} +0.90°$ (c=1, chloroform).

EXAMPLE 9

In the same flask as in Example 1, 20% sulfuric acid (10 ml) was charged, and dl-3-acetoxy-2-propargyl-3-methyl-4-cyclopentenone (1.92 g) was dropwise added thereto in 1 hour while keeping the inner temperature at 0° C. After completion of the dropwise addition, the resultant mixture was stirred at the same temperature as above for 3 hours. The reaction mixture was subjected to post-treatment and purification as in Example 1 to give 1.38 g of 4-hydroxy-2-propargyl-3-methyl-2-cyclopentenone. Yield, 91%.

EXAMPLE 10

In the same flask as in Example 1, there were charged 3-acetoxy-2-n-pentyl-3-methyl-4-cyclopentenone (2.24 g), tetrahydrofuran (10 ml) and 20% sulfuric acid (10 ml), and the resultant mixture was stirred at 30° to 50° C. for 6 hours. After completion of the reaction, the reaction mixture was subjected to post-treatment and purification as in EXAMPLE 1 to give 1.55 g of 4-hydroxy-2-n-pentyl-3-methyl-2-cyclopentenone. Yield, 85%.

EXAMPLE 11

In the same manner as in Example 1 but using 3-acetoxy-2-allyl-4-cyclopentenone (1.8 g) instead of 3-acetoxy-2-allyl-3-methyl-4-cyclopentenone, the reaction was carried out. The reaction mixture was subjected to post-treatment as in Example 1 and purified by column chromatography using a mixture of toluene and ethyl acetate (5:4) as an eluent to give 1.15 g of 2-allyl-4-hydroxy-2-cyclopentenone. Yield, 83.5%.

EXAMPLE 12

In the same manner as in Example 1 but using 2-allyl-3-propionyloxy-3-methyl-4-cyclopentenone (2.08 g) instead of 3-acetoxy-2-allyl-3-methyl-4-cyclopentenone, the reaction was carried out. The reaction mixture was subjected to post-treatment as in Example 1 and purified to give 1.26 g of 2-allyl-4-hydroxy-3-methyl-2-cyclopentenone. Yield, 83%.

EXAMPLE 13

In the same flask as in Example 1, 10% aqueous hydrochloric acid (10 ml) and dioxane (10 ml) were charged, and 2-allyl-3-acetoxy-3-methyl-4-cyclopentenone (1.94 g) was dropwise added thereto in 2 hours while keeping the inner temperature at 0° to 10° C. After completion of the dropwise addition, the resultant mixture was stirred at the same temperature as above for 3 hours. The reaction mixture was subjected to post-treatment and purification as in Example 1 to give 1.37 g of 2-allyl-3-methyl-4-hydroxy-2-cyclopentenone. Yield, 90%.

In the same manner as above but using acetone (10 ml) instead of dioxane (10 ml), there were obtained 1.38 g of 2-allyl-3-methyl-4-hydroxy-2-cyclopentenone. Yield, 90.5%.

EXAMPLES 14 TO 17

In the same manner as in Example 1 but using the 2-acyloxy-4-cyclopentenone (II) as shown in Table 3 instead of dl-3-acetoxy-2-allyl-3-methyl-4-cyclopentenone, the reaction was carried out. (In Example 17, the reaction was carried out as in Example 10.) The results are shown in Table 3.

TABLE 3

| Example No. | Starting 2-acyloxy-4-cyclopentenone (II) | | | | Objective 4-hydroxy-2-cyclopentenone (I) | |
|---|---|---|---|---|---|---|
| | R | $R_1$ | $R_2$ | Amount (g) | Amount (g) | Yield (g) |
| 14 | —OCOCH$_3$ | —CH$_3$ | —CH$_2$C≡CH | 1.92 | 1.19 | 79.5 |
| 15 | —OCOCH$_3$ | —CH$_3$ | —n-C$_3$H$_7$ | 1.96 | 1.33 | 86.5 |
| 16 | —OCOCH$_3$ | —CH$_3$ | —CH$_3$ | 1.68 | 1.04 | 82.5 |
| 17 | —OCOCH$_3$ | —H | —n-C$_5$H$_{11}$ | 1.78 | 1.14 | 84 |

EXAMPLE 18

In the same flask as in Example 1, there were charged 3-acetoxy-2-allyl-3-methyl-4-cyclopentenone (3.0 g), water (10 g) and acetic acid (5 g), and the resultant mixture was stirred under reflux for 10 hours. After completion of the reaction, the reaction mixture was concentrated under reduced pressure and extracted three times with methyl isobutyl ketone (60 ml). The organic layers were combined together, washed with water and dried over magnesium sulfate. After concentration under reduced pressure, the residue was purified by column chromatography to give 1.95 g of 2-allyl-4-hydroxy-3-methyl-2-cyclopentenone. Yield, 83%.

What is claimed is:

1. A process for producing a compound of the formula:

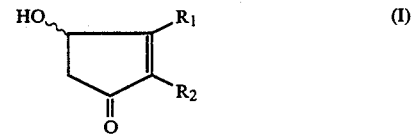

wherein $R_1$ is a hydrogen atom, a $C_{1-12}$ alkyl group or a $C_{1-12}$ alkenyl group, and $R_2$ is a $C_{1-12}$ alkyl, alkenyl or alkynyl group, which comprises treating a compound of the formula:

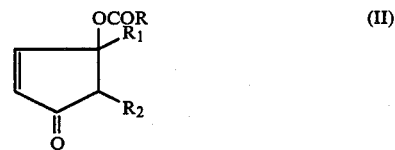

wherein $R_1$ and $R_2$ are each as defined above and R is a hydrogen atom or a $C_{1-6}$ alkyl group, in a reaction medium comprising from 1 to 50 moles of water and from 0.2 to 50 moles of an inorganic or organic acid, each to one mole of compound (II).

2. The process according to claim 1, wherein the reaction is carried out at a temperature of $-20°$ to 110° C.

3. The process according to claim 1, wherein R is methyl or propionyl, $R_1$ is hydrogen or methyl and $R_2$ is allyl methyl, n-propyl, propylene, n-pentyl, or propargyl.

4. The process according to claim 1, wherein the starting compound (II) is optically active.

5. The process according to claim 1, wherein the produced compound (I) is substantially a racemic mixture.

6. The process according to claim 1, wherein the inorganic acid is chosen from hydrochloric acid, sulfuric acid, nitric acid, phosphoric acid, chloric acid, polyphosphoric acid and boric acid.

7. The process according to claim 1, wherein the organic acid is chosen from toluenesulfonic acid, methane-sulfonic acid and acetic acid.

8. A process for producing a compound of the formula:

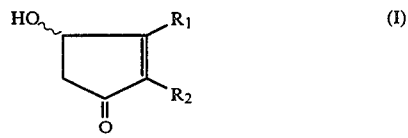

wherein $R_1$ is a hydrogen atom, a $C_{1-12}$ alkyl group or a $C_{1-12}$ alkenyl group, and $R_2$ is a $C_{1-12}$ alkyl, alkenyl or alkynyl group, which comprises treating a compound of the formula:

$$\underset{O}{\overset{OCOR}{\underset{\|}{\diagup}}\underset{R_2}{\overset{R_1}{\diagdown}}} \quad (II)$$

wherein $R_1$ and $R_2$ are each as defined above and R is a hydrogen atom or a $C_{1-6}$ alkyl group, in a reaction medium comprising water and acid selected from the group consisting of hydrochloric acid, sulfuric acid, nitric acid, phosphoric acid, chloric acid, polyphosphoric acid, boric acid, toluenesulfonic acid, methane-sulfonic acid and acetic acid.

9. The process according to claim 8, wherein the starting compound (II) is optically active.

10. The process according to claim 8, wherein the produced compound (I) is substantially a racemic mixture.

* * * * *